United States Patent [19]

Nomura et al.

[11] Patent Number: 5,235,238
[45] Date of Patent: Aug. 10, 1993

[54] ELECTRODE-SEPARATED PIEZOELECTRIC CRYSTAL OSCILLATOR AND METHOD FOR MEASUREMENT USING THE ELECTRODE-SEPARATED PIEZOELECTRIC CRYSTAL OSCILLATOR

[75] Inventors: Toshiaki Nomura, Higashichikuma; Tohru Yamada, Matsudo, both of Japan

[73] Assignee: Dainabot Company, Limited, Japan

[21] Appl. No.: 832,789

[22] Filed: Feb. 7, 1992

Related U.S. Application Data

[63] Continuation-in-part of Ser. No. 564,374, Aug. 8, 1990, abandoned.

[30] Foreign Application Priority Data

Aug. 10, 1989 [JP] Japan ................................ 1-205590

[51] Int. Cl.$^5$ ............................................ H01L 41/08
[52] U.S. Cl. ................................... 310/349; 73/19.03
[58] Field of Search ....................... 310/321, 323, 349; 73/24.01, 19.03, 588, 589; 324/652, 727

[56] References Cited

U.S. PATENT DOCUMENTS 1,860,529  5/1932  Cady ................................ 310/321
4,666,547  5/1987  Snowden et al. ................. 310/321
4,789,804 12/1988  Karube et al. ................... 310/321

OTHER PUBLICATIONS

"Handbook of Piezoelectric Crystals" by J.Buchanan, Philco for Wright Air Dev. Ctr., Dec. 1954.
"Analytical Uses of Piezoelectric Crystals: A Review," by G. Guilbault et al., 1988.
"A Quartz Plate with Coupled Liquid Column as a Variable Resonator" by F. Fox et al. Proceedings of I.R.E., Jan. 1942.

*Primary Examiner*—Mark O. Budd
*Assistant Examiner*—Thomas M. Dougherty
*Attorney, Agent, or Firm*—Scully, Scott, Murphy & Presser

[57] ABSTRACT

Herein disclosed is a device for determining the concentration of a substance in a solution by making use of a quartz oscillator. In the device, at least one of a plurality of electrodes for applying an electrical voltage to a crystal wafer is separated from the crystal wafer, and the space between the separated electrode and the crystal wafer is filled with a conductive substance. The electrode-separated piezoelectric crystal oscillator thus obtained can be made more highly accurate, smaller-sized and more inexpensive.

2 Claims, 2 Drawing Sheets

ELECTRODE-SEPARATED PIEZOELECTRIC CRYSTAL OSCILLATOR AND METHOD FOR MEASUREMENT USING THE ELECTRODE-SEPARATED PIEZOELECTRIC CRYSTAL OSCILLATOR

This application is a continuation-in-part of copending application Ser. No. 564,374, filed Aug. 8, 1990 now abandoned.

FIELD OF THE INVENTION

The present invention relate to both an electrode-separated piezoelectric crystal oscillator whose oscillating frequency is measurable even when immersed in a solution, and a method for detecting a substance in a solution or determining the concentration of the substance in a solution by using the electrode-separated piezoelectric crystal oscillator.

BACKGROUND OF THE INVENTION

It has been reported in the prior art that a quartz oscillator may be used to measure the concentration of a substance in a solution. Specifically, it has been reported that the concentration of a substance in a solution may be determined by measuring the change in oscillation frequency due to a change in mass on the surface of the quartz oscillator.

For example, one of the present inventors used the method for assay of a substance in a solution by measuring the change in the oscillator frequency during the direct binding of the substance to the quartz oscillator, and have determined the concentration of silver ion in an aqueous solution by taking advantage of the fact that the silver ion in the solution will electrodeposit on the electrode of the oscillator naturally (e.g., T. Nomura, et al., Anal. Chem. Acta, 169, 257 (1985)).

On the other hand, Muramatsu, et al., used the method for assay of a substance in a solution by binding the substance indirectly to a quartz oscillator, and have assayed IgG in the solution by using the piezoelectric crystal with Protein A immobilized thereon (e.g., H. Muramatsu, et al., Anal. Chem., 59, 2760 (1987)). It was also reported in Japanese Patent Laid Open No. 62-64934 to immobilize an antibody on the surface of the crystal and detect a specific microbe by the antigen-antibody reaction.

On the other hand, an electrode-separated piezoelectric crystal oscillator having its electrode separated from the crystal wafer was reported by W. G. Cady (e.g., W. G. Cady, J. Gen. Appl. Phys., 7, 237 (1936)). What has been reported by W. G. Cady is to compare the oscillating frequency in the case where the electrode is separated from the crystal wafer with the frequency in the unseparated case. However, W. G. Cady has failed to show the capability of assay of a specific substance or its concentration by using the separate electrode-separated piezoelectric crystal oscillator.

The quartz oscillator used in the prior art for measuring a substance is of the type in which a thin film of an electrode is adhered on the crystal wafer. The electrode is applied to the crystal wafer by vacuum evaporation or by an electro-plating process, etc. The electrode layer thus formed will cause unstable oscillation of the oscillator if excessively thick, and will be liable to come off if excessively thin, reducing its practicability. Therefore, the thickness of the electrode layer has to be precisely controlled by troublesome operations. Moreover, it is necessary that a lead wire be attached to the electrode on the crystal wafer in order to apply an electrical voltage to the electrode from an oscillation circuit. This limits the reduction of the size of the electrode. Since the quartz oscillator is used in a solution, on the other hand, the oscillation frequency due to only the binding of a substance to be assayed cannot be accurately measured if the electrode is dissolved or comes off.

Therefore, this makes it necessary to use a noncorrosive precious metal such as gold, platinum, or palladium as the material for the electrode. Thus, the fabrication of the quartz oscillator of the prior art has problems of troublesome processes, high costs, and difficulties in fabricating products of uniform quality and small size. Hence, such oscillators having high production costs cannot be generally used as measurement elements of disposable type, so that it has to be repeatedly used for the measurements. Since, in this case, the troublesome operations are required for rinsing (or reactivating) the oscillator after each measurement, the electrode cannot be avoided from erosion or the like when at the rinsing step, even if it is made of the above-specified noncorrosive material. As a result, the responsiveness of the oscillator is degraded after each measurement, reducing the reproducibility of the measurements. Thus, it is difficult to measure many samples for a short time period, and the reliability of the assay results obtained has a problem.

Since the quartz oscillator of the prior art is united with the electrode, the weight of the oscillator is increased by the electro-deposition of the substance coexisting in the solution on the electrode surface, thus causing a problem of interfering with the accurate measurement of the frequency change.

SUMMARY OF THE INVENTION

An object of the present invention is to overcome the disadvantages of the prior art and to provide both an inexpensive quartz oscillator having a measurement accuracy better than that of the prior art, and a method for measuring the concentration of a substance in a solution by using the quart oscillator.

The present invention overcomes the problems of the prior art by using an electrode-separated piezoelectric crystal oscillator. The present invention relates to an electrode-separated piezoelectric crystal oscillator which is characterized in that at least one of a plurality of electrodes for applying an electrical voltage to a crystal wafer is separated from the crystal wafer, and the crystal wafer is characterized by the thickness shear mode. Moreover, the present invention relates to an electrode-separated piezoelectric crystal oscillator which is characterized in that (i) at least one of a plurality of electrodes for applying an electrical voltage to a crystal wafer is separated from the crystal wafer, in that (ii) the space between the separated electrode and the crystal wafer is filled with a conductive substance, and in that (iii) the crystal wafer is characterized by the thickness shear mode.

The quartz oscillator of the present invention provides a method for detecting a substance to be assayed or for determining the concentration of the substance by binding the substance directly or indirectly to the crystal wafer and by measuring the variation in the oscillating frequency of the quartz oscillator. The present invention also relates to a measurement method based on such principle. The present invention also provides an electrode-separated piezo-electric crystal oscillator in which one or both of two electrodes for applying an electrical voltage to a crystal wafer are separated from the crystal wafer and in which the space between the separated electrodes and the crystal wafer is filled with a conductive substance. Moreover, the present invention further provides an electrode-separated oscillator in which the electrode for applying an electrical voltage to a crystal wafer is separated from the crystal wafer and in which the space between the separated electrode and the crystal wafer is filled with a conductive substance and/or a substance to be assayed.

DETAILED DESCRIPTION OF THE PREFERRED EMBODIMENTS

Figure 1:
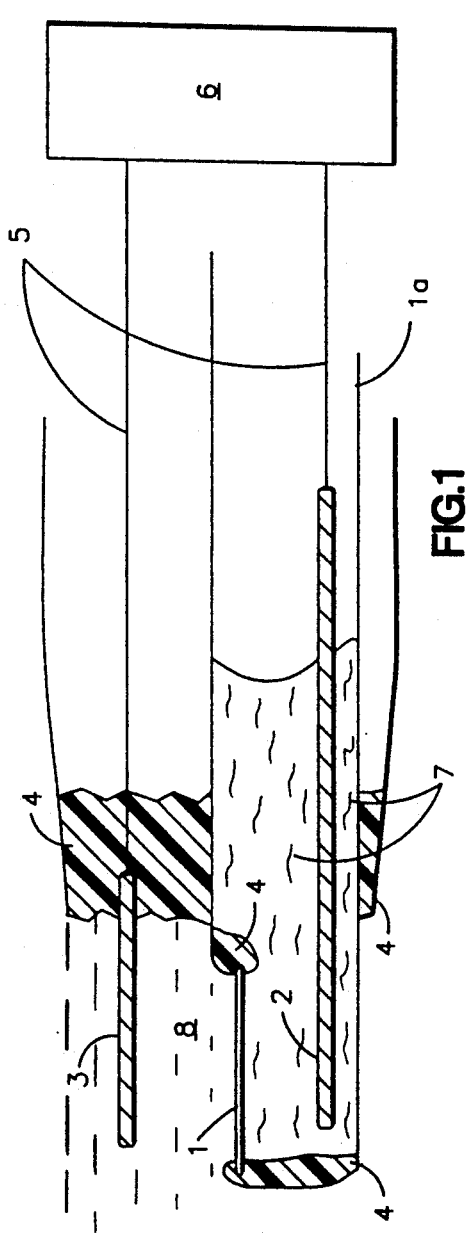
FIG. 1 is a section showing an example of an electrode-separated piezoelectric crystal oscillator.

An electrolytic solution can be suitably used as a conductor which can fill the space between the separate electrode and the crystal wafer of the electrode-separated piezoelectric crystal oscillator according to the present invention. The conductive substance may be a solution containing an electrolyte dissolved in a suitable solvent, a liquid metal, or a semisolid such as a jelly or gel.

As the electrolyte and the like, constituent of such conductive substance, there may be exemplified by salts of alkaline metal such as sodium or potassium, salts of alkaline earth metal such as magnesium or calcium, salts or metal such as tin, lead, iron, nickel, cobalt, manganese, chromium, copper or zinc, ammonium salts, and organic ammonium salt. The other component of the salt may be exemplified by hydrohalide, halogenate, perhalogenate, hydride, carbonate, bicarbonate, nitrate, sulfate, sulfite, borate, cyanate, a salt of an organic acid such as formic acid, acetic acid, propionic acid, trifluoroacetic acid or benzoic acid, or a salt of an organic sulfonic acid such as methane-sulfonic acid, benzenesulfonic acid or paratoluenesulfonic acid.

As the solvent for dissolving the above-specified electrolyte and the like, there may be exemplified by water, methanol, ethanol, propanol, acetone, dioxane, acetonitrile, tetrahydrofuran, N,N-dimethylformamide, dimethylsulfoxide or polypropylene carbonate, or their mixture. The concentration of the electrolyte and the like in the solvent can be so changed in accordance with the kind of electrolyte used that the optimum measurement result may be obtained. In order to form the electrolyte or the like into the jelly or gel state, there can be used sodium alginate, carboxymethyl cellulose, polyacryl amide, hydroxypropylmethyl cellulose or silicone, copolymer of ethylene-areinic acid, polyester, polyvinylalcohols, dextran, cross-linked dextran, agar, or their derivatives. The conductive substance in addition to the above-specified ones may be exemplified by a low or high molecular weight organic conductive material or chemical compound.

The preferable electrolyte in the present invention may be exemplified by potassium chloride, sodium chloride, potassium bromide, sodium bromide, potassium phosphate, sodium phosphate, sodium hydrogen phosphate, potassium nitrate, hydrochloric acid, hydrobromic acid, nitric acid, sulfuric acid, potassium hydroxide, sodium hydroxide, potassium cyanide, potassium acetate, sodium acetate, triethylammonium chloride, ammonium chloride, or ammonium phosphate.

The electrode material to be used in the present invention can be exemplified by gold, platinum, or palladium but may preferably be a more inexpensive metal such as copper, iron, cobalt, nickel, silver, or zinc, their suitable alloys, carbon, organic conductive materials or conductive ceramics.

The number of electrodes of the present invention may be two or more, as required. Moreover, the shape of the electrodes may be linear, planar, circular, or tooth-shaped, as required.

The piezoelectric crystal wafer to be used in the present invention can be prepared by a mechanical or chemical treatment. The shape and size of the crystal wafer can be suitably selected in accordance with the purpose of the use and the feasibility of fabrication. In the present invention, moreover, a plurality of crystal wafers can be used.

The quartz oscillator of the present invention may be partially or wholly coated or deposited directly or indirectly with a substance having an affinity to the various substances according to the purpose of the use. The coating or depositing method to be used may be a physical or chemical method, or a combination thereof. The method for applying the aforementioned substance having an affinity to the quartz oscillator may be a method using an adhesive, a method using a chemical binding agent such as glutaraldehyde, carbodiimide, cyanogen halide, isothiocyanate, azide, epoxide, divinyl sulfone, cyanurate chloride, isonitrile, acid anhydride, mercury chloride, bromoacetyl bromide, epihalohydrin, 2,3-dihalopropanol, or a method using natural adsorption. Moreover, the aforementioned binder may be made to act directly upon the quartz oscillator, or indirectly, for example, after its surface is treated with alkylsilane.

The substance having an affinity to the various substances used may be exemplified by a physically or chemically binding substance such as chelating agent, protein, sugar, glycoprotein, mucopolysaccharide, liquid, glycolipid, peptide, cells, tissues, biometabolites, or bioproducts. For example, there can be exemplified by polyclonal antibody, monoclonal antibody, antiserum, antigen, enzyme, substrate, hormone, hormone receptor, bioreceptor, nucleic acid and its complementary strand, agglutinin, mitogen, lectin, blood components, or a substance, adsorbing other substances by a molecular sieving effect or by an iron-exchanging capacity. More specifically, there can be enumerated a chelating agent such as EDTA, an antibody against various antigens such as anti-CEA antibody, NAD, various enzyme inhibitors, hormones such as insulin, insulin receptor, concanavalin A, protein A, lysine, n-butyl-p-benzoate, arginine, trypsin, DNA, or RNA.

A variety of substances can be assayed by the electrode-separated piezoelectric crystal. The specimens, to which the present measurement can be applied, range widely, for example, a variety of aqueous solutions to be ordinarily assayed or organic solutions. For example, there can be enumerated an ordinary aqueous solution containing a variety of ions, industrial liquid waste, liquids containing trace components in laboratories, blood, ascitic fluid, pleural exudate, spinal fluid, urine, fluid extracted from tissues, cell culture, or fluid extracted from the last. In the present invention, the quartz oscillator can be removably fixed on the device of the present invention by various manners. The fixing method of the quartz oscillator on the device of the present invention may be an ordinary one so long as it does not adversely affect the measurements. Such methods include those using a water-proof, insulating material such as glass, silicone resin, vinyl resin, polyethylene, polypropylene, polystyrene, fluorine contained resin, rubber or an organic high-molecular adhesive.

When the electrode-separated piezoelectric crystal oscillator of the present invention is used, the substance to be measured can be assayed accurately. Moreover, the electrode-separated piezoelectric crystal oscillator of the present invention can be easily fabricated at a reasonable cost so that it finds useful applications in the field requiring disposable oscillators.

EXAMPLES

The examples of the present invention will be described in the following with reference to FIGS. 1 to 5. However, it should be understood that the examples are not intended to limit the scope of the present invention.

EXAMPLE 1

FIG. 1 shows an example of the electrode-separated piezoelectric crystal oscillator of the present invention.

In the electrode-separated piezoelectric crystal oscillator shown in FIG. 1, a crystal wafer 1 is fixed on a substrate 1a by a silicone resin 4, and two separate electrodes 2 and 3 are arranged in its vicinity. Here, the crystal wafer 1 can be easily removed and replaced with another. The electrodes 2 and 3 are connected through individual lead wires 5 to an oscillatory circuit 6. The quartz oscillator is so filled with a conductive substance 7 as to immerse the electrode and to bring one side of the crystal wafer 1 into contact with the substance 7. When in use, the quartz oscillator is so filled with a sample solution 8 as to immerse the electrode 3 in the sample solution 8. This sample solution is in contact with the other side of the crystal wafer 1.

Figure 2:
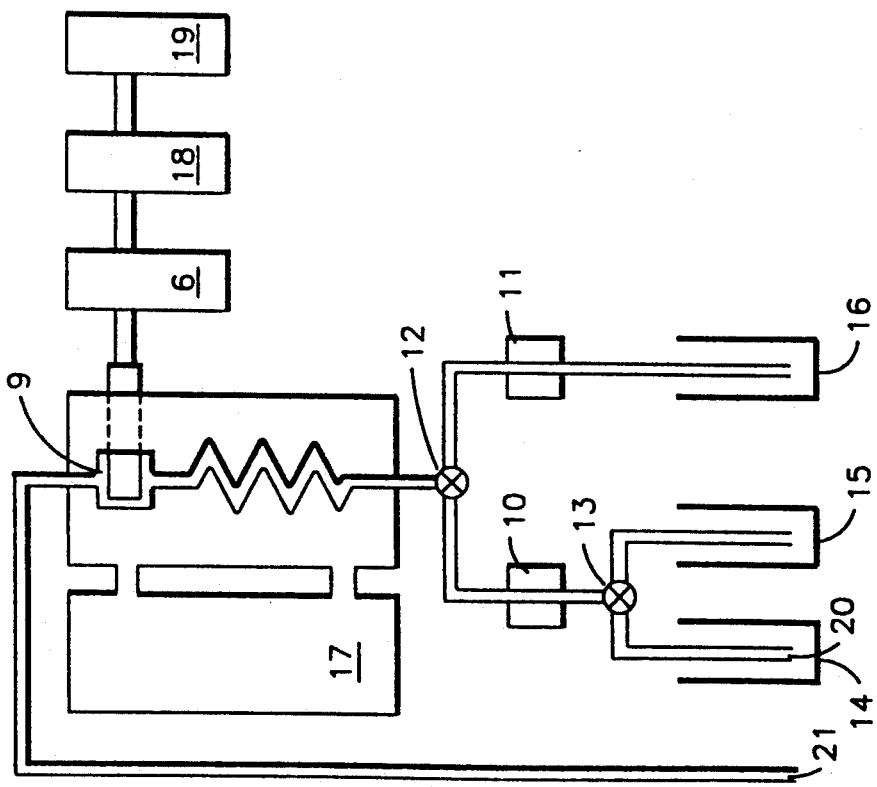
FIG. 2 is a block diagram showing the whole structure of an example of a measurement device using the electrode-separated piezoelectric crystal oscillator.

FIG. 2 is a schematic diagram showing one example of the measurement system using the electrode-separated piezoelectric crystal oscillator of the present invention. For example, the electrode-separated piezoelectric crystal oscillator shown in FIG. 1 is installed in a flow type measurement cell 9. Peristaltic pumps 10 and 11 are used, and a three-way valve 12 and a two-way valve 13 are changed over to introduce the solution into the measurement cell 9 from solution containers 14, 15, and 16. Water of a constant temperature (e.g., 20.0±0.1° C.) is supplied from a thermostatic bath 17 to the outside of the measurement cell 9 to hold the temperatures of the sample solution 8 and the crystal wafer 1 at the constant level. The oscillating frequency is measured by a frequency counter 18 connected with the aforementioned oscillator 6 and is recorded with a recorder 19.

EXAMPLE 2: Determination of the Concentration of Sulfate

Ions by Using the ElectrodeSeparated

Piezoelectric Crystal Oscillator

The method for measuring the concentration of sulfate ions by using the aforementioned device will be described in the following.

An electrode-separated piezoelectric crystal oscillator having the same structure as that of the oscillator of FIG. 1 was prepared by using a 9-MHz crystal wafer having nothing fixed on its surface and was installed in the measurement cell 9. The peristaltic pumps 10 and 11 and the valves 12 and 13 were regulated to introduce an acetate solution of 0.01M from the solution container 14 and a barium nitrate solution of 0.01M (acidified by 0.0M acetic acid) from the solution container 16 both at a flow velocity of 2.5 ml/min. into the measurement cell 9. In this state, an oscillatory frequency (FI) was measured. Next, the valve 13 was changed over to introduce a standard solution of sulfate ions (i.e., a solution of sodium sulfate acidified by 0.01M acetic acid) from the solution container 15 for 5 min.

Figure 3:
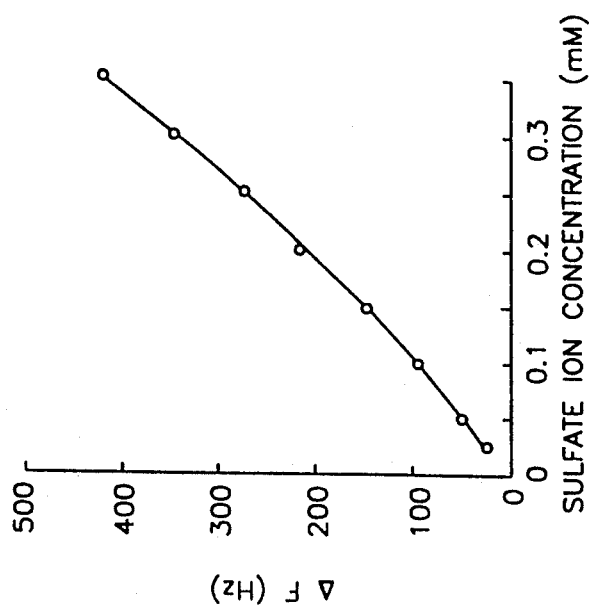
FIG. 3 is a diagram showing the calibration curve of sulfate ion according to Example 2 of the present invention.

At this time, the sulfate ions directly adsorbed as barium sulfate on the crystal wafer, so that the oscillating frequency was decreased. The valve 13 was changed over to introduce the solution of acetic acid again from the solution container 14, and an oscillating frequency (F2) was measured. By repeating similar operations, the changes (i.e., $F = F1 - F2$) in the response of the oscillator to the various concentrations of the sulfate ions were measured. FIG. 3 shows the relation between the sulfate ion concentration and the changes in the responses. The responses varied in dependence upon the sulfate ion concentration. Therefore, the sulfate ion concentration could be determined in terms of the responses by introducing a sample solution of an unknown concentration by similar methods.

EXAMPLE 3: Determination of the Concentration of

$\beta_2$-Microglobulin by Using the Electrode-Separated

Piezoelectric Oscillator

The method for measuring the concentration of $\beta_2$-microglobulin (which will be simply referred to as "$\beta_2$-M") by using a device similar to the aforementioned one will be described in the following.

A crystal wafer of 18MHz was dipped for an hour in an acetone solution of aminopropyl ethoxysilane of 5% and was rinsed with water. After this, the crystal wafer was dipped again for three hours in an aqueous solution of glutaraldehyde of 5% and was rinsed with water. Next, the crystal wafer was immersed for one hour in a solution of anti-$\beta_2$-M antibody of 3 mg/ml. After a rinsing operation with water, the crystal wafer was dried in a desiccator. The crystal wafer on which the anti-$\beta_2$-M antibody was fixed was installed in the position of the crystal wafer 1 of FIG. 1 to prepare an electrode-separated piezoelectric crystal oscillator. This oscillator was installed in the measurement cell 9. The valve 13 and the peristaltic pump 10 were regulated to introduce a blank liquid (i.e., saline buffered with sodium phosphate of 0.05M at pH 6.5) at a flow rate of 8 ml/min. from the solution container 14 into the measurement cell, and the oscillatory frequency (FI) was measured.

Figure 4:
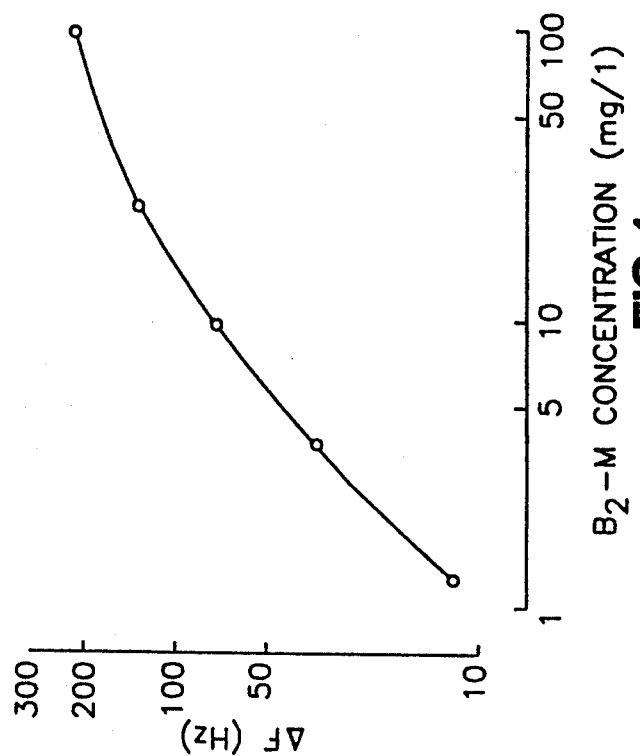
FIG. 4 is a diagram showing the calibration curve of $\beta_2$-M according to Example 3 of the invention.

Next, the valve 13 was changed over to sample 100 μl of standard solution of $\beta_2$-M, and the valve 13 was returned to the initial position. At this time, an inlet 20 and an outlet 21 were connected to circulate 10 ml of the solution for 30 min. The $\beta_2$-M was uniquely bound to the antibody which had been fixed to the surface of the crystal wafer so that the frequency was decreased. The oscillating frequency (Fl) after the circulation of 30 min. was measured, and the change ( F=Fl−F2) in the response was calculated. FIG. 4 shows the relation between the $\beta_2$-M concentration and the response. The response was changed in dependence upon the $\beta_2$-M concentration. Therefore, the $\beta_2$-M concentration could be measured in terms of the response by supplying a body fluid sample such as blood or urine in a similar manner.

EXAMPLE 4

Figure 5:
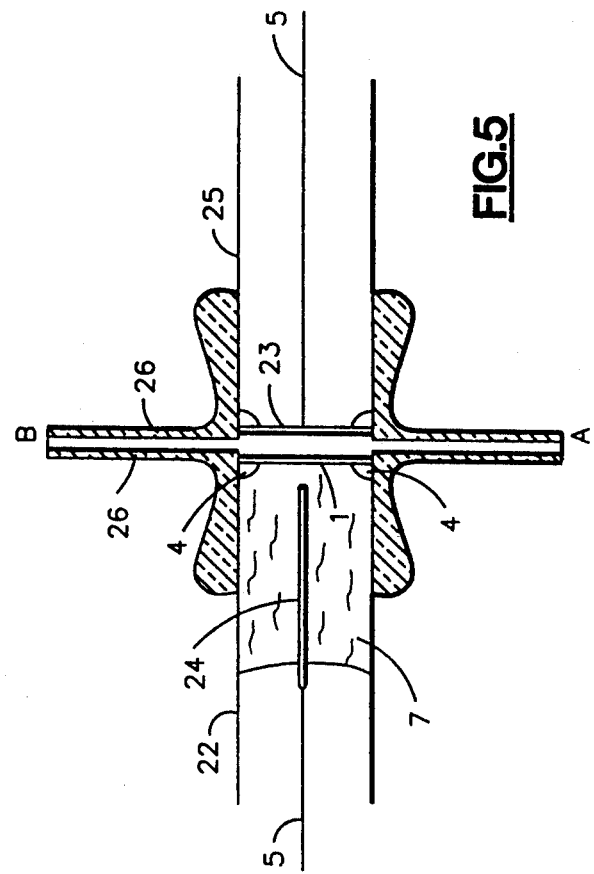
FIG. 5 is a section showing an example of the electrode-separated piezoelectrode crystal oscillator.

FIG. 5 shows another example of the electrode-separated piezoelectric crystal oscillator of the present invention.

In the electrode-separated piezoelectric crystal oscillator shown in FIG. 5, the crystal wafer is fixed on a substrate 22 with the silicone resin 4. An electrode 23 is so disposed as to face the crystal wafer 1, and an electrode 24 is disposed separately through the conductive substance 7 in the vicinity of the crystal wafer 1. The substrate 22 and a substrate 25 are so arranged as to face the crystal wafer 1 and the electrode 23 respectively through a connecting device 26. The lead wires 5 are individually connected with the electrodes 23 and 24 and guided to the oscillatory circuit 6. In the case the present electrode-separated piezoelectric crystal oscillator is to be used, the sample solution is supplied from a connected portion A to a connected portion B.

In the device thus constructed, the substrates 22 and 25 may preferably be made of glass pipes, and the connecting device 26 may preferably be made of a glass pipe The substrates 22 and 25 have their ground contacts. Not only can trace samples be assayed, but larger samples can also be assayed, by using the electrode-separated piezoelectric crystal; however, it is preferred to assay trace samples. Moreover, the aforementioned device is advantageous in that the sample to be assayed can be continuously introduced into the device, so that it can assay many kinds of samples by the simple operations. According to the device, moreover, the crystal wafer can be replaced without any difficulty, so that one device can be used to handle a number of samples.

According to the present invention, a quartz oscillator to be used for analyzing a substance in a solution can be provided with ease and at a reasonable cost.

What is claimed is:

1. An electrode-separated piezoelectric crystal oscillator (which comprises) comprising:
    a crystal wafer characterized by the thickness shear mode; and
    at least two electrodes for applying an electric voltage to said crystal wafer, said at least two electrodes being spaced apart from said crystal wafer, wherein the space between one of said separated electrode and said crystal wafer is filled with a liquid or semi-solid conductive substance.

2. A method for detecting an analyte in a sample or determining the concentration of said analyte comprising the steps of:
    (a) obtaining a first oscillation frequency measurement of an electrode-separated piezoelectric crystal oscillator, said first frequency measurement taken at a first or second electrode, each of said first and second electrodes separated from said crystal oscillator by a respective first and second gap, wherein one of said gaps is filled with a liquid or semi-solid electrically conductive substance;
    (b) filling the other of said gaps with said sample;
    (c) binding said analyte contained in said sample directly or indirectly to the electrode-separated piezoelectric crystal oscillator;
    (d) obtaining a second oscillation frequency measurement of said electrode-separated piezoelectric crystal oscillator; and
    (e) detecting the quality or quantity of said analyte by determining the frequency difference between said first and second oscillation frequency measurements.

* * * * *

UNITED STATES PATENT AND TRADEMARK OFFICE
CERTIFICATE OF CORRECTION

PATENT NO.   : 5,235,238
DATED        : August 10, 1993
INVENTOR(S)  : Toshiaki Nomura, et al.

It is certified that error appears in the above-indentified patent and that said Letters Patent is hereby corrected as shown below:

Column 1, line 10:  "abandened"  should read as --abandoned--

Column 2, line 42:  "quart"  should read as --quartz--

Column 6, line 4:  "ElectrodeSeparated"  should read as --Electrode-Separated--

Column 6, line 18:  "0.0M"  should read as --0.02M--

Signed and Sealed this

Twentieth Day of June, 1995

Attest:

BRUCE LEHMAN

Attesting Officer        Commissioner of Patents and Trademarks